(12) United States Patent
Chapman et al.

(10) Patent No.: US 6,395,899 B2
(45) Date of Patent: May 28, 2002

(54) ELECTRONEGATIVELY SUBSTITUTED PYRIMIDINES AND INTERMEDIATES LEADING TO RNFX

(75) Inventors: Robert Dale Chapman, Ridgecrest, CA (US); Ba Van Nguyen, Tewksbury, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/911,640

(22) Filed: Jul. 23, 2001

Related U.S. Application Data

(62) Division of application No. 09/505,127, filed on Feb. 16, 2000, now Pat. No. 6,310,204.

(51) Int. Cl.[7] .................... C07D 239/04; C07D 239/06; C07D 239/10; C07C 211/11
(52) U.S. Cl. ............................ 544/322; 564/82; 149/92
(58) Field of Search ........................ 544/322; 564/82; 149/92

(56) References Cited

PUBLICATIONS

Miller, R.S., Research on New Energetic Materials Research Society Symposium Proceeding, Nov. 27–30, vol. 418, pp 3–14, 1995, Material Research Society(1996), Pitsburgh, PA.*

Chapman et al., Journal of Organic Chemistry, vol. 63, 1566–1570, 1998.*
Chapman et al., Journal of Organic Chemistry, vol. 64, 960–1965, 1999.*
Hansch et al., Chemical Reviews, vol. 91(2), 165–195, 1991.*

* cited by examiner

*Primary Examiner*—Richard L. Raymond
*Assistant Examiner*—Venkataraman Balasubramanian
(74) *Attorney, Agent, or Firm*—Anthony J. Serventi

(57) ABSTRACT

Calculated performance improvements are expected from a particularly new class of compounds, geminal-bis (difluoramino)-substituted heterocyclic nitramines, when formulated into explosives and propellants. This invention involves novel and nonintuitive methods for the preparation of certain derivatives of 2,2-bis(difluoramino)-N-nitro-1,3-propanediamine which are suitable precursors leading to 5,5-bis(difluoramino)hexahydro-1,3-dinitropyrimidine (RNFX). The invention also involves novel and nonintuitive methods for the preparation of RNFX, a specific member of a general class of compounds with the substructure 2,2-bis (difluoramino)-N-nitro-1,3-propanediamine. RNFX is produced by the use of key intermediates, including tetrahydropyrimidin-5(4H)-ones, which allow formation of the target structural subcomponent, 2,2-bis(difluoramino)-N-nitro-1,3-propanediamine, and a more specific substructure of 2,2-bis(difluoramino)-N,N'-dinitro-1,3-propanediamine. In addition, this invention involves 5,5-bis (difluoramino)hexahydropyrimidine derivatives, related geminal-bis(difluoramino)alkylene derivatives, and novel precursors to these new derivatives, by the use of certain novel key intermediates.

17 Claims, No Drawings

ELECTRONEGATIVELY SUBSTITUTED PYRIMIDINES AND INTERMEDIATES LEADING TO RNFX

CROSS-REFERENCE TO RELATED APPLICATIONS

This application is being filed as a Divisional Application in accordance with 37 C.F.R. 1.53(b). The Parent Application of this Divisional Application is application Ser. No. 09/505,127 filed Feb. 16, 2000 which is now U.S. Pat. No. 6,310,204.

BACKGROUND OF THE INVENTION

1. Field of the Invention

This invention involves the calculated performance improvements expected from a particularly new class of compounds, geminal-bis(difluoramino)-substituted heterocyclic nitramines, when formulated into explosives and propellants. Further, this invention involves 5,5-bis (difluoramino)hexahydropyrimidine derivatives, related geminal-bis(difluoramino)alkylene derivatives, and novel precursors to these new derivatives, by the use of certain key intermediates which allow formation of this target structural subcomponent.

2. Description of the Related Art

The calculated performance improvements expected from geminal-bis(difluoramino)-substituted heterocyclic nitramines when formulated into explosives and propellants has been reported. [Miller, *Materials Research Society Proceedings* 1996, 418, 3] One example of a highly desirable structure, described by Miller, is a derivative of 5,5-bis (difluoramino)hexahydro-1,3-dinitropyrimidine which has the following formula:

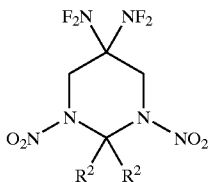

wherein $R^2$ is selected from the group consisting of hydrogen, alkyl, and substituted alkyl. The highly desirable structure, given the acronym RNFX by Miller, exists when $R^2$ is hydrogen.

Methodology for preparing a geminal-bis(difluoramino)-substituted nitrogenous heterocycle has been reported by Chapman et al. [*Journal of Organic Chemistry* 1998, 63, 1566], who describe the preparation of 3,3,7,7-tetrakis (difluoramino)octahydro-1,5-bis(4-nitrobenzenesulfonyl)-1,5-diazocine; this intermediate has been converted to the corresponding nitramine, 3,3,7,7-tetrakis(difluoramino) octahydro-1,5-dinitro-1,5-diazocine, given the acronym HNFX [Chapman et al, *Journal of Organic Chemistry*, 1999, 64, 960]. However the preparation of cyclic derivatives of 2,2-bis(difluoramino)-N,N'-dinitro-1,3-propanediamine in which the nitramine components are linked with a single-carbon bridge, such as RNFX, has not been previously described.

SUMMARY OF THE INVENTION

This invention involves novel and nonintuitive methods for the preparation of certain derivatives of 2,2-bis (difluoramino)-N-nitro-1,3-propanediamine which are suitable precursors leading to RNFX. However, the synthesis of certain examples of this class of compounds is difficult and nonintuitive. The certain examples that are particularly synthetically difficult are molecules that incorporate the geminal-bis(difluoramino)alkylene [$C(NF_2)_2$] component and the nitramine component [$N-NO_2$] in close proximity, especially when separated by only a methylene ($CH_2$) link in order to maintain a low fuel-to-oxidizer component ratio and concomitantly high oxygen balance in the product molecule. The invention also involves novel and nonintuitive methods for the preparation of RNFX, a specific member of a general class of compounds with the substructure 2,2-bis (difluoramino)-N-nitro-1,3-propanediamine. RNFX is produced by the use of key intermediates which allow formation of the target structural subcomponents, 2,2-bis (difluoramino)-N-nitro-1,3-propanediamine and a more specific substructure of 2,2-bis(difluoramino)-N,N'-dinitro-1,3-propanediamine, which has the following structure:

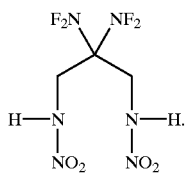

Also, this invention comprises certain unprecedented nitramides and nitramines suitable for conversion to RNFX and a variety of other difluoramino-substituted heterocyclic nitramines. An important aspect of the present invention is the substitution on heterocyclic precursors' nitrogen atoms and intermediate nitramides' nitrogen atoms. The nitrogen atoms of heterocyclic precursors (such as pyrimidines) must be suitably substituted, or "protected," during the process of difluoramination to allow this process to proceed to geminal-bis(difluoramino)alkylene derivatives. Without suitable protection of proximate multiple nitrogens, especially those separated from reacting carbonyl sites by a short bridge, such as methylene, the process of difluoramination of ketone intermediates does not proceed to geminal-bis (difluoramino)alkylene derivatives. The result is mono (difluoramino)alkylene derivatives or no reaction at all.

An object of this invention is to create a novel explosive and propellant involving geminal-bis(difluoramino)-substituted heterocyclic nitramines.

Another object of this invention is to create a novel method of producing 5,5-bis(difluoramino)hexahydro-1,3-dinitropyrimidine using electronegatively substituted pyrimidines and other novel intermediates leading to RNFX.

BRIEF DESCRIPTION DRAWINGS

Not Applicable.

DETAILED DESCRIPTION OF THE INVENTION

The collection of pyrimidine intermediates disclosed in this invention which are suitable for eventual conversion to RNFX must allow formation of a tetrahydropyrimidin-5 (4H)-one having the following structure:

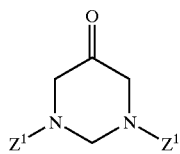

wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl. Further, the regioisomer of fluoroarenesulfonyl is selected from the group consisting of 2-,3- and 4-fluoro-substituted arenesulfonyl, the regioisomer of cyanoarenesulfonyl is selected from the group consisting of 2-,3- and 4-cyano-substituted arenesulfonyl and the regioisomer of nitroarenesulfonyl is selected from the group consisting of 2-,3- and 4-nitro-substituted arenesulfonyl.

In the invention, a tetrahydropyrimidin-5(4H)-one is a necessary precursor to a 5,5-bis(difluoramino) hexahydropyrimidine, based on the known conversion of ketone carbonyl groups by reaction with difluoramine or difluorosulfamic acid in the presence of a strong acid. The nitrogen-protecting groups chosen for the new pyrimidine intermediates and precursors are certain sulfonyl substituents. The particular sulfonyl substituents are chosen from a group that favorably affects the basicity of the pyrimidine nitrogens to make them less basic than the oxygen sites in the pyrimidine intermediates, in order to allow difluoramination of the carbonyl oxygens to proceed to geminal-bis (difluoramino)alkylene derivatives.

Suitable intermediates leading to tetrahydropyrimidin-5 (4H)-ones include hexahydro-5-pyrimidinols (including their oxygen-protected derivatives) and hexahydro-5-(methylene)pyrimidines. These novel N-sulfonylpyrimidine derivatives include hexahydro-5-pyrimidinols having the structure:

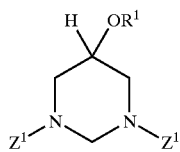

wherein $Z^1$ is selected from the group consisting of halosulfonyl, polyhaloalkanesulfonyl, polyhaloarenesulfonyl, a regiolsomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl. Further, the regioisomer of fluoroarenesulfonyl is selected from the group consisting of 2-,3- and 4-fluoro-substituted arenesulfonyl, the regioisomer of cyanoarenesulfonyl is selected from the group consisting of 2-,3- and 4-cyano-substituted arenesulfonyl and the regioisomer of nitroarenesulfonyl is selected from the group consisting of 2-,3- and 4-nitro-substituted arenesulfonyl.; and wherein $R^1$ is selected from the group consisting of hydrogen and an alcohol-protecting group.

The novel N-sulfonylpyrimidine derivatives also include hexahydro-5-(methylene)pyrimidines having the following structure:

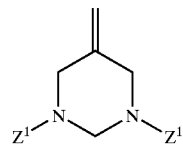

wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl. Further, the regioisomer of fluoroarenesulfonyl is selected from the group consisting of 2-,3- and 4-fluoro-substituted arenesulfonyl, the regioisomer of cyanoarenesulfonyl is selected from the group consisting of 2-,3- and 4-cyano-substituted arenesulfonyl and the regioisomer of nitroarenesulfonyl is selected from the group consisting of 2-,3- and 4-nitro-substituted arenesulfonyl.

In the preferred embodiment, a hexahydro-5-(methylene) pyrimidine is utilized as the intermediate leading to a tetrahydropyrimidin-5(4H)-one. In the present invention, the production of hexahydro-5-(methylene)pyrimidines is accomplished as follows:

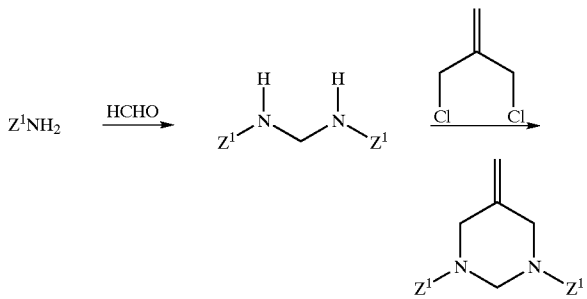

wherein $Z^1$ is selected from the group consisting of halosulfonyl, polyhaloalkanesulfonyl, polyhaloarenesulfonyl, a regioisomer of cyanoarenesulfonyl, polycyanoarenesulfonyl, a regioisomer of nitroarenesulfonyl, and polynitroarenesulfonyl. Further, the regioisomer of fluoroarenesulfonyl is selected from the group consisting of 2-,3- and 4-fluoro-substituted arenesulfonyl, the regioisomer of cyanoarenesulfonyl is selected from the group consisting of 2-,3- and 4-cyano-substituted arenesulfonyl and the regioisomer of nitroarenesulfonyl is selected from the group consisting of 2-,3- and 4-nitro-substituted arenesulfonyl.

Hexahydro-5-pyrimidinols and hexahydro-5-(methylene) pyrimidines are suitable intermediates that can be converted to tetrahydropyrimidin-5(4H)-one precursors. For example, hexahydro-5-(methylene)pyrimidines are converted to tetrahydropyrimidin-5(4H)-ones by ozonlysis of the exomethylene substituent. Next, these precursors are converted to novel 5,5-bis(difluoramino)hexahydropyrimidines and other geminal-bis(difluoramino)alkylene derivatives by difluoramination.

In the preferred embodiment of the invention, the general path of the reaction, after the formation of a tetrahydropyrimidin-5(4H)-one, is illustrated as follows:

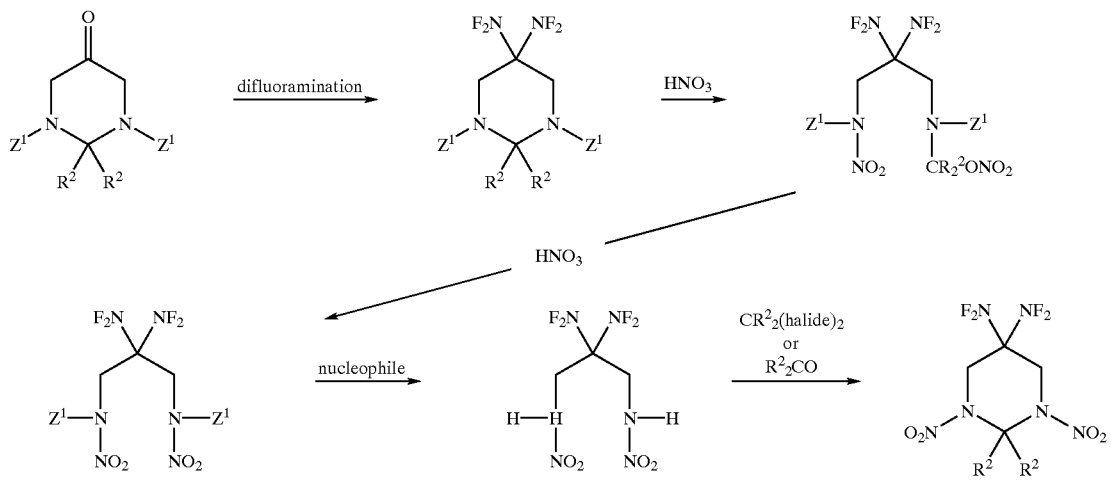

wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regiolsomer of cyanoarenesulfonyl, polycyanoarenesulfonyl, a regioisomer of nitroarenesulfonyl, and polynitroarenesulfonyl. Further, the regioisomer of fluoroarenesulfonyl is selected from the group consisting of 2-,3- and 4-fluoro-substituted arenesulfonyl, the regioisomer of cyanoarenesulfonyl is selected from the group consisting of 2-,3- and 4-cyano-substituted arenesulfonyl and the regioisomer of nitroarenesulfonyl is selected from the group consisting of 2-,3- and 4-nitro-substituted arenesulfonyl.; and wherein $R^2$ is selected from the group consisting of hydrogen, $C_1$–$C_2$ alkyl, protected hydroxymethyl and 1,2 ethanediyl.

In another embodiment of the invention, the reaction may also be accomplished using a carbonyl, rather than the $R^2$ groups illustrated above. That general path is illustrated as follows:

polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl. Further, the regioisomer of fluoroarenesulfonyl is selected from the group consisting of 2-,3- and 4-fluoro-substituted arenesulfonyl, the regioisomer of cyanoarenesulfonyl is selected from the group consisting of 2-,3- and 4-cyano-substituted arenesulfonyl and the regioisomer of nitroarenesulfonyl is selected from the group consisting of 2-,3- and 4-nitro-substituted arenesulfonyl.

Tetrahydropyrimidin-5(4H)-ones suitable for conversion to 5,5-bis(difluoramino)hexahydropyrimidines are substituted on the nitrogens (positions 1 and 3) by electron-withdrawing sulfonyl substituents. The particular sulfonyl substituents are chosen from a specific group that imparts lower basicity to the nitrogens than to the oxygen in the tetrahydropyrimidin-5(4H)-ones. Therefore, the substituent causes the nitrogens to have acid dissociation constants ($pK_a$) of the (protonated) conjugate acid forms of the nitrogen sites to be less than that of the ketones, typically about −7.

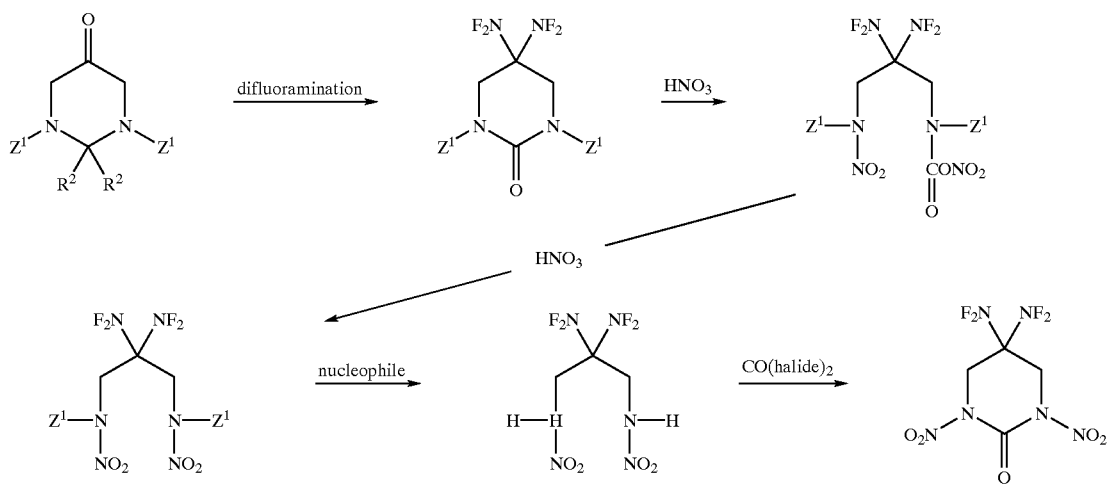

wherein $Z^1$ is selected from the group consisting of halosulfonyl, polyhaloalkanesulfonyl, The sulfonyl substituents may include alkanesulfonyl, halosulfonyl, or arenesulfonyl substituents, but the arenesulfonyl must have electron-withdrawing substituents on the phenyl rings. For example, the nitro group ($NO_2$) is a suitable electron-withdrawing subsitituent. Any single or multiple electron-withdrawing subsitituent(s) that collectively lower(s) the basicity of the arenesulfonyl-protected nitrogens below that of the oxygen in corresponding tetrahydropyrimidin-5(4H)-ones is (are) suitable. Similarly, alkanesulfonyl protecting groups may be electronegatively substituted to impart the same property on the protected nitrogens. In general, the sulfonyl substituent must have an inductive substituent constant ($\sigma_I$ or F) of a value greater than that of unsubstituted benzenesulfonyl, approximately 0.58. Such electronegatively substituted pyrimidines are unprecedented.

The geminal-bis(difluoramino)alkylene derivatives must be susceptible to nitrolysis to form N-protected nitramines (i.e. nitramides) and the intermediate nitramides must be susceptible to deprotection to form desired nitramine intermediates. Those intermediates then undergo cyclization by reaction with aldehydes or other alkylating reagents to form difluoramino-substituted heterocyclic nitramines.

In the final step of the process, 2,2-bis(difluoramino)-N, N'-dinitro-1,3-propanediamine intermediate is reacted with an electrophile or alkylating reagent, such as aldehyde, alkylene dihalide, aldehyde equivalent or alkylene di(pseudohalide), to undergo cyclization to a desired difluoramino-substituted heterocyclic nitramine. A cyclic 2,2-bis(difluoramino)-N,N'-dinitro-1,3-propanediamine is the same as a generic 5,5-bis(difluoramino)hexahydro-1,3-dinitropyrimidine when the cyclization is effected by a group containing only a single-carbon linkage between the two nitrogens (positions 1 and 3). This linkage may have additional substituents, but the pyrimidine linkage contains N—C—N atoms directly bonded.

The process of making RNFX consists of nitrolyzing the cyclic 2,2-bis(difluoramino)-N,N'-disulfonyl-1,3-propanediamine with nitric acid or other nitronium source to prepare a 2,2-bis(difluoramino)-N,N'-dinitro-N,N'-disulfonyl-1,3-propanediamine. This nitrolysis may proceed via a 2,2-bis(difluoramino)-N-nitro-1,3-propanediamine intermediate, if a chemical linkage bridging the precursor's sulfonamide nitrogens is retained by one of the nitrogens upon nitrolysis. The resulting 2,2-bis(difluoramino)-N,N'-dinitro-N,N'-disulfonyl-1,3-propanediamine is then subjected to nucleophilic displacement of the sulfonyl protecting group. In 2,2-bis(difluoramino)propanamine derivatives, this deprotection is relatively facile, and appropriate nucleophiles include a wide variety of oxygen, nitrogen and other heteroatom derivatives, examples of which include water, alcohols and amines. The resulting deprotected nitramine, 2,2-bis(difluoramino)-N,N'-dinitro-1,3-propanediamine, is then reacted with a difunctional electrophile suitable for cyclizing the bisnitramine. A variety of electrophiles are suitable for this purpose, including aldehydes, dihaloalkanes, alkyl pseudohalides, other typical alkylating reagents, acylating reagents, and sulfonating reagents. The use of formaldehyde as the cyclizing reagent produces the simple hexahydropyrimidine product (RNFX).

In the successful examples cited below, 4-nitrobenzenesulfonyl was used as a role model nitrogen-protecting sulfonyl group to prepare electronegatively substituted pyrimidines as intermediates and precursors leading to geminal-bis(difluoramino)alkylene derivatives. A wide variety of other heretofore unknown pyrimidine derivatives suitable for conversion, successively, to tetrapyrimidin-5-(4H)-ones and then to geminal-bis(difluoramino)alkylene derivatives becomes apparent from a review of known electron-withdrawing properties of sulfonyl substituents, such as reviewed by Hansch et al., *Chemical Reviews* 1991, 91, 165; these require that inductive substituent constants, A or F, are greater than approximately 0.58, the value known for unsubstituted benzenesulfonyl. Thus, other suitable electronegatively substituted pyrimidines include those protected on nitrogen by chlorosulfonyl; fluorosulfonyl; cyanosulfonyl; polyhaloalkanesulfonyls, such as difluoromethanesulfonyl, trifluoromethanesulfonyl, and all perfluoroalkanesulfonyls; arenesulfonyls appropriately substituted such that collective effects of substituents on the arene impart the desired electronegativity on the arenesulfonyl, including, but not limited to, nitrobenzenesulfonyl (all isomers) and all polynitrobenzenesulfonyls.

Arenesulfonyl substituents may be based on arenes other than benzene, including various aromatic heterocycles, such as azines. Individual substituents on the arenesulfonyl of electronegativity comparable to or greater than that of nitro impart suitable electronegativity to the sulfonyl subsitituents to make suitable pyrimidine intermediates. The collective effect of multiple electronegative substituents of electronegativity less than that of nitro would also impart, collectively, the same necessary property of lowered basicity; examples include polyhaloarenesulfonyl and polycyanoarenesulfonyl protecting groups; other examples are apparent from compilations of quantitative inductive effects, such as Hansch et al. (op. cit.).

In the successful examples cited below, 4-nitrobenzenesulfonyl was used as a model nitrogen-protecting sulfonyl group to prepare 2,2-bis(difluoramino)-N,N'-dinitro-N,N'-bis(4-nitrobenzenesulfonyl)-1,3-propanediamine intermediates susceptible to nucleophilic N-desulfonation and subsequent cyclization by appropriate electrophiles. Based on the known general susceptibility of N-alkyl-N-nitrosulfonamides to nucleophilic N-desulfonation, it would be apparent that a variety of other N-sulfonyl subsituents are suitable for the present process of preparing 2,2-bis(difluoramino)-N,N'-dinitro-1,3-propanediamine and subsequent cyclized derivatives, including alkanesulfonyl, arenesulfonyl (including heteroarenesulfonyl), and halosulfonyl protecting groups.

In the successful examples cited below, a cyclic 2,2-bis(difluoramino)-N,N'-disulfonyl-1,3-propanediamine precursor [specifically, 5,5-bis(difluoramino)hexahydro-1,3-bis(4-nitrobenzenesulfonyl)pyrimidine] contained methylene ($CH_2$) as a bridging link between sulfonamide nitrogens of the reactant; the methylene bridge was susceptible to nitrolysis to an N-nitratomethyl substituent which was also nitrolyzed, forming an N-nitrosulfonamide. Based on the known susceptibility to nitrolysis of "substituted methylene" linkages bridging heterocyclic nitrogens, other 5,5-bis(difluoramino)hexahydro-1,3-disulfonylpyrimidines substituted in the 2-position are also suitable reactants for the nitrolysis step generating 2,2-bis(difluoramino)-N,N'-dinitro-1,3-propanediamine derivatives. The 2-position substituents that remain feasible within the present process include a wide variety of alkyl, aryl (including heteroaryl) and cyclic alkyl (including heterocyclic alkyl) substituents. The class of feasible examples thus includes perhydro-2,2'-bipyrimidines and a variety of other bicyclic systems linked to the 2-position of the reactant 5,5-bis(difluoramino) hexahydro-1,3-disulfonylpyrimidine.

In the successful examples cited below, a formaldehyde equivalent generated in situ during nitrolysis of an N-nitratomethyl substituent was used to recyclize 2,2-bis(difluoramino)-N,N'-dinitro-1,3-propanediamine to form RNFX. Based on the known general reactivity of primary nitramines with aldehydes (under acid catalyzed conditions) and other electrophiles, the present process is extensible to the formation of other cyclic 2,2-bis(difluoramino)-N,N-dinitro-1,3-propanediamine derivatives via cyclization with alternative electrophiles. For example, 1,3-propanediamines are known to condense with glyoxal to form perhydro-2,2'-bipyrimidines; 2,2-bis(difluoramino)-N,N'-dinitro-1,3- propanediamine thus forms 5,5,5',5'-tetrakis (difluoramino) perhydro-1,1',3,3'-tetranitro-2,2'-bipyrimidine with glyoxal.

Although the description above contains many specificities, these should not be construed as limiting the scope of the invention but as merely providing an illustration of the presently preferred embodiment of the invention. Thus the scope of this invention should be determined by the appended claims and their legal equivalents.

EXAMPLES

Example 1

Preparation of hexahydro-1,3-bis(4-nitrobenzenesulfonyl)-5-pyrimidinol

A 37% aqueous solution of formaldehyde (1.34 mL) was added dropwise to a stirred solution of 1,3-diamino-2-hydroxypropane (Aldrich Chemical Co., 95% purity, 1.5 g, 17 mmol) in 8 mL of water over 30 minutes at room temperature. After stirring at room temperature for 3 days, the solvent was removed via distillation to give a light yellow solid, hexahydro-5-pyrimidinol.

A solution of hexahydro-5-pyrimidinol (1.0 g, 9.8 mmol) and sodium carbonate (1.04 g, 9.8 mmol) in 10 mL of water in a 250 mL round bottom flask was stirred with a magnetic stir bar for 10 minutes. A solution of 4-nitrobenzenesulfonyl chloride (4.4 g, 19.8 mmol) in 10 mL of toluene was added dropwise over a period of 30 minutes. The reaction mixture formed a white suspended solid. A mixture of 100 mL of water and 20 mL of toluene was added to the reaction mixture and stirred overnight. The reaction mixture was filtered and the solid was washed with 100 mL of toluene, then with 100 mL of water. The solid was dried at room temperature under reduced pressure to give 4.4 g (95%) of crude product, hexahydro-1,3-bis(4-nitrobenzenesulfonyl)-5-pyrimidinol. [$^1$H NMR (DMSO-d$_6$): δ2.29 (s, 1H), 2.84, 3.47 {AB q of d, J=12.4(3.8) Hz, 12.4(7.9) Hz, 4H}, 3.30 (m, 1H), 4.46, 5.07 (AB q, J=12.5 Hz, 2H), 5.31 (s, 1H), 8.11, 8.41 (AB q, J=8.7 Hz, 8H); $^{13}$C NMR (DMSO-d$_6$): δ50.0, 59.8, 60.6, 124.6, 128.9, 143.3, 150.1].

Example 2

Preparation of hexahydro-5-(methylene)-1,3-bis(4-nitrobenzenesulfonyl)pyrimidine A suspended mixture of 4-nitrobenzenesulfonamide (2.0 g, 9.9 mmol) and potassium carbonate (0.68 g, 4.9 mmol) in 100 mL water was stirred and heated at 70° C. until the reaction mixture turned clear. Aqueous 37% formaldehyde (0.2 mL, 4.9 mmol) was added and the mixture heated at 70° C. for 3 days. The reaction mixture was concentrated by removal of water via rotary evaporation at reduced pressure. The reaction mixture was neutralized to pH 7 with hydrochloric acid. The resulting solid was filtered and washed with water to give 0.7 g (18%) of methylenebis(4-nitrobenzenesulfonamide) [$^1$H NMR (acetone-d$_6$): δ2.82 (s, 2H), 4.86 (m, 2H), 8.07, 8.35 (AB q, J=8.9 Hz, 8H); $^{13}$C NMR (acetone-d$_6$) δ53.0, 125.2, 129.1, 148.4, 151.0]. The yield of this reaction ranged from 10–30%. A mixture of methylenebis(4-nitrobenzenesulfonamide) (1.0 g, 2.4 mmol), potassium carbonate (0.66 g, 4.8 mmol), and 3-chloro-2-(chloromethyl)-1-propene (0.3 g, 2.4 mmol) in 150 mL of acetonitrile was stirred and heated at reflux under a nitrogen atmosphere for 20 h. The solvent was removed under reduced pressure, and the remaining solid was chromatographed (silica gel-ethyl acetate) to give 0.84 g (75%) of solid, hexahydro-5-(methylene)-1,3-bis(4-nitrobenzenesulfonyl)pyrimidine [$^1$H NMR (acetone-d$_6$): δ3.90 (s, 4H), 4.95 (m, 2H), 5.00 (s, 2H), 8.18,8.44 (AB q of t, J=9.0(2.2) Hz, 8H); $^{13}$C NMR (acetone-d6): δ51.0, 61.7, 116.2, 125.3, 130.6, 133.6, 144.6, 151.6].

Example 3

Preparation of tetrahydro-1,3-bis(4-nitrobenzenesulfonyl)pyrimidin-5(4H)-one

A stream of ozone in oxygen was bubbled into a solution of hexahydro-5-(methylene)-1,3-bis(4-nitrobenzenesulfonyl)pyrimidine (0.6 g, 1.3 mmol) in 150 mL acetone at −78° C. (dry ice-acetone bath) until a blue color persisted for 5 minutes. The reaction was stirred for 15 minutes under a nitrogen atmosphere. Next, 2.0 mL of dimethyl sulfide was added. After stirring for 10 minutes, the solvent was removed and the solid dried under reduced pressure to give 0.5 g (83%) of tetrahydro-1,3-bis(4-nitrobenzenesulfonyl)pyrimidin-5(4H)-one. [$^1$H NMR (acetone-d$_6$): δ3.95 (s, 4H), 5.25 (s, 2H), 8.20, 8.48 (AB q, J=9.0 Hz, 8H); $^{13}$C NMR (DMSO-d$_6$): δ53.8, 58.8, 124.8, 129.3, 141.9, 150.4, 196.2].

Example 4

Preparation of 2,2-bis(difluoramino)-N,N'-bis(difluoraminomethyl)-N,N'-(4-nitrobenzenesulfonyl)-1,3-propanediamine Difluoramine (2.2 g, 41.5 mmol) was absorbed into a mixture of 3.0 mL fuming sulfuric acid (30% SO$_3$) plus 100 mL of trichlorofluoromethane in a temperature range of −15 to +5° C. Tetrahydro-1,3-bis(4-nitrobenzenesulfonyl) pyrimidin-5(4H)-one (0.255 g, 0.54 mmol) was added via a solid addition funnel with another 15 mL of trichlorofluoromethane to wash out the funnel. After 3 h stirring at −15° C., the reaction mixture was poured onto ice. The mixture was basified with aqueous sodium carbonate to pH 6 and then extracted with dichloromethane. The solvent was removed from this extract by rotary evaporation and the residue was redissolved in chloroform and chromatographed on silica gel, eluting successively with chloroform (two fractions) and dichloromethane (three fractions). Fraction #2, eluted by chloroform, contained a mixture of 2,2-bis(difluoramino)-N,N'-bis(difluoraminomethyl)-N,N'-(4-nitrobenzenesulfonyl)-1,3-propanediamine [$^1$H NMR (chloroform-d): δ4.39 (s), 5.09 (t), 8.12, 8.44 (AB q, J=8.9 Hz); $^{19}$F NMR (chloroform-d): δ30.59 (s), 44.86 (t, J=22.9 Hz)] and N,N-bis(difluoraminomethyl)-4-nitrobenzenesulfonamide [$^1$H NMR (chloroform-d): δ5.03 (t, J=22.6 Hz, 4H), 8.09, 8.42 (AB q, J=8.9 Hz, 8H); $^{19}$F NMR (chloroform-d): δ43.53 (t,J=22.4 Hz)].

Example 5

Preparation of 5,5-bis(difluoramino)hexahydro-1,3-bis(4-nitrobenzenesulfonyl)pyrimidine and 5,5-bis(difluoramino)-1-(difluoraminomethyl)hexahydro-3-(4-nitrobenzenesulfonyl)pyrimidine The same reaction as described in Example 4 is performed. Elution of chromatography Fraction #3 with dichloromethane produced a mixture containing predominantly 5,5-bis(difluoramino)hexahydro-1,3-bis(4-nitrobenzenesulfonyl)pyrimidine [$^1$H NMR (dichloromethane-d$_2$-chloroform-d): δ3.98 (s, 4H), 4.98 (s, 2H), 8.07, 8.42 (AB q, J=9.0 Hz, 8H); $^{13}$C NMR (dichloromethane-d$_2$-chloroform-d): δ44.3 (m, J=9.0 Hz), 60.4, 89.7 (m), 125.3, 129.5, 144.0, 151.4; $^{19}$F NMR (dichloromethane-d$_2$-chloroform-d): δ27.27] plus minor amounts of 5,5-bis(difluoramino)-1-(difluoraminomethyl) hexahydro-3-(4-nitrobenzenesulfonyl)pyrimidine [$^{19}$F NMR (dichloromethane-d$_2$-chloroform-d): δ21.65, 28.15

(AB q, J=610 Hz, 4F), 45.38 (t, J=20.8 Hz, 2F)], N-(difluoraminomethyl)-4-nitrobenzenesulfonamide [$^{19}$F NMR (dichloromethane-d$_2$-chloroform-d): δ39.86 (td, J=22.6, 7.6 Hz)] and N,N-bis(difluoraminomethyl)-4-nitrobenzenesulfonamide.

Example 6

Preparation of 5,5-bis(difluoramino)hexahydro-1,3-bis(4-nitrobenzenesulfonyl)pyrimidine The same reaction as in Example 4 is performed. Elution of chromatography Fraction #4 with dichloromethane produced effectively pure 5,5-bis(difluoramino)hexahydro-1,3-bis(4-nitrobenzenesulfonyl) pyrimidine.

Example 7

Preparation of 2,2-bis(difluoramino)-N-(nitratomethyl)-N-nitro-N,N'-bis(4-nitrobenzenesulfonyl)-1,3-propanediamine 5,5-Bis(difluoramino)hexahydro-1,3-bis(4-nitrobenzenesulfonyl)pyrimidine is dissolved in a large excess of ca. 98% nitric acid. Nitrolysis of the methylene bridge in this reactant is conveniently followed by $^{19}$F NMR spectrometry. Nitrolysis initially produces 2,2-bis(difluoramino)-N-(nitratomethyl)-N'-nitro-N,N'-bis(4-nitrobenzenesulfonyl)-1,3-propanediamine [$^{1}$H NMR (HNO$_3$): δ4.53 (s), 5.09 (s), 5.88 (s), 8.42, 8.78 (AB q, J 9.0 Hz, 4H, N-aryl), 8.43, 8.70 (AB q, J=9.0 Hz, 4H, N'-aryl); $^{13}$C NMR (HNO$_3$): δ44.2, 45.8, 60.6, 90.8, 125.6, 128.6, 131.3, 143.1, 146.6, 150.5, 151.6; $^{19}$F NMR (HNO$_3$): δ29.39].

Example 8

Preparation of 2,2-bis(difluoramino)-N,N'-dinitro-1,3-propanediamine

Nitrolysis of the intermediate formed in Example 7 replaces the N-nitratomethyl substitituent with N-nitro. The reaction rates of the successive nitrolysis steps are expectedly influenced by the concentration of reactants—the sulfonamides and nitric acid. With a proper proportion of reactants, the next step of the sequence occurs spontaneously: 2,2-bis(difluoramino)-N,N'-dinitro-N,N'-bis(4-nitrobenzenesulfonyl)-1,3-propanediamine is adventitiously N-desulfonated by the water contained in the concentrated nitric acid, forming 2,2-bis(difluoramino)-N,N'-dinitro-1,3-propanediamine, which does not accumulate but combines spontaneously with the formaldehyde equivalent generated in this nitrolysis; as described in Example 9.

Example 9

Preparation of 5,5-bis(difluoramino)hexahydro-1,3-dinitropyrimidine (RNFX)

Under the conditions of nitrolysis of 2,2-bis(difluoramino)-N-(nitratomethyl)-N'-nitro-N,N'-bis(4-nitrobenzenesulfonyl)-1,3-propanediamine in ca. 98% nitric acid, the liberated formaldehyde equivalent becomes available for cyclization of the N-desulfonated bis(primary nitramine), 2,2-bis(difluoramino)-N,N'-dinitro-1,3-propanediamine. The cyclization occurred spontaneously at room temperature, consuming the 2,2-bis(difluoramino)-N,N'-dinitro-1,3-propanediamine intermediate and forming 5,5-bis(difluoramino)hexahydro-1,3-dinitropyrimidine (RNFX) [$^{1}$H NMR (CD$_3$CN): δ4.85 (s, 4H), 6.06 (s, 2H); $^{1}$H NMR (acetone-d$_6$): δ5.07 (s, 4H), 6.31 (s, 2 H); $^{13}$C NMR (CD$_3$CN): δ45.3 (m, J 6 Hz), 60.6 (s) (not all carbons detected due to low S/N); $^{19}$F NMR (CD$_3$CN): δ29.67; $^{19}$F NMR (acetone-d$_6$): δ29.31)].

What is claimed is:

1. A method of preparing a cyclic 2,2-bis(difluoramino)-N,N'-dinitro-1,3-propanediamine which comprises the steps of:

reacting with an electrophile, a 2,2-bis(difluoramino)-N,N'-dinitro-1,3-propanediamine having a formula:

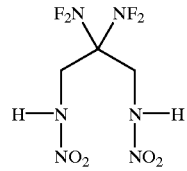

and producing a cyclic 2,2-bis(difluoramino)-N,N'-dinitro-1,3-propanediamine having a formula selected from the group consisting of:

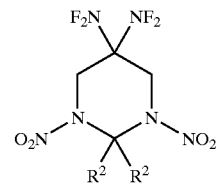 and 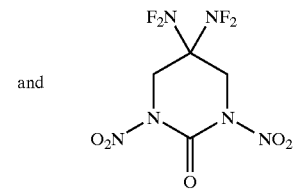

wherein R$_2$ is selected from the group consisting of hydrogen, alkyl, and substituted alkyl.

2. The method according to claim 1 wherein said electrophile is selected from the group consisting of aldehyde, aldehyde equivalent, alkylene dihalide, and alkylene di(pseudohalide).

3. The method according to claim 2 wherein said aldehyde is selected from the group consisting of formaldehyde, glyoxal, a nitrate ester of formaldehyde and a nitrate ester of glyoxal.

4. The method according to claim 1, wherein said reacting with an electrophile takes place at a temperature ranging from about −80° C. to about 120° C.

5. The method according to claim 1, further comprising the steps of:

reacting a 2,2-bis(difluoramino)-N-nitro-N,N'-disulfonyl-1,3-propanediamine with a nitronium source and producing said 2,2-bis(difluoramino)-N,N'-dinitro-1,3-propanediamine.

6. The method according to claim 5 wherein said nitronium source is selected from the group consisting of nitric acid, a nitronium salt, and a covalent nitryl derivative.

7. The method according to claim 5, wherein said reacting with a nitronium source takes place at a temperature ranging from about −80° C. to about 120° C.

8. The method according to claim 5, further comprising the steps of:

reacting with a nitronium source a 5,5-bis(difluoramino)hexahydro-1,3-disulfonylpyrimidine having a formula selected from the group consisting of:

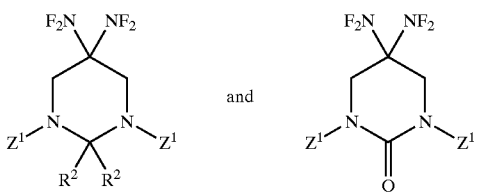

and recovering a 2,2-bis(difluoramino)-N'-nitro-N,N'-disulfonyl-1,3-propanediamine having a formula selected from the group consisting of:

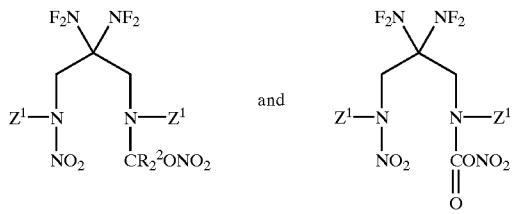

wherein $R^2$ is selected from the group consisting of hydrogen, alkyl, and substituted alkyl; and wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl.

9. The method according to claim 8 wherein said nitronium source is selected from the group consisting of nitric acid, a nitronium salt, and a covalent nitryl derivative.

10. The method according to claim 8 wherein said 5,5-bis(difluoramino)hexahydro-1,3-disulfonylpyrimidine is a 2-substituted pyrimidine.

11. The method according to claim 8, wherein said reacting with a nitronium source takes place at a temperature ranging from about −80° C. to about 120° C.

12. The method according to claim 8, further comprising the steps of:

performing difluoramination, in the presence of a strong acid, on a tetrahydropyrimidin-5(4H)-one having a formula selected from the group consisting of:

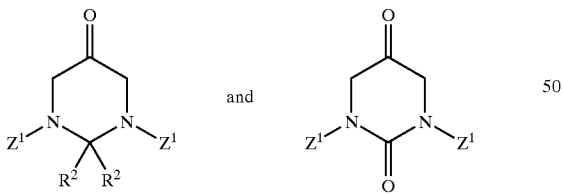

and recovering said 5,5-bis(difluoramino)hexahydro-1,3-disulfonylpyrimidine;

wherein $R^2$ is selected from the group consisting of hydrogen, $C_1$–$C_2$ alkyl, and protected hydroxymethyl and 1,2 ethanediyl; and wherein $Z^1$ of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl.

13. The method according to claim 12, wherein said difluoramination takes place at a temperature ranging from about −40° C. to about 100° C.

14. The method according to claim 12 wherein said strong acid is selected from the group consisting of difluorosulfamic acid and sulfuric acid, difluorosulfamic acid, anhydrous sulfuric acid, fluorosulfonic acid, and any combination thereof.

15. A pyrimidine having a formula selected from the group consisting of:

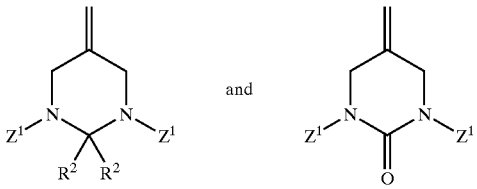

wherein $R^2$ is selected from the group consisting of hydrogen, $C_1$–$C_2$ alkyl, protected hydroxymethyl and 1,2 ethanediyl; and wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl.

16. A propanediamine having a formula:

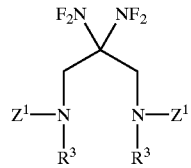

wherein $R^3$ is selected from the group consisting of hydrogen, $C_1$–$C_2$ alkyl, and 1-(difluoramino)alkyl; and wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl.

17. A propanediamine having a formula:

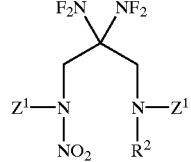

wherein $R^2$ is selected from the group consisting of hydrogen, $C_1$–$C_2$ alkyl, substituted alkyl, halo, and nitro; and wherein $Z^1$ is selected from the group consisting of halosulfonyl, polyhaloalkanesulfonyl, polyhaloarenesulfonyl, a regioisomer of fluoroarenesulfonyl, polyhaloarenesulfonyl, a regioisomer of cyanoarenesulfonyl, polycyanoarenesulfonyl, a regioisomer of nitroarenesulfonyl, and polynitroarenesulfonyl.

* * * * *